United States Patent
Yuan et al.

(10) Patent No.: US 7,943,385 B2
(45) Date of Patent: *May 17, 2011

(54) METHODS FOR ASSAYING PERCENTAGE OF GLYCATED HEMOGLOBIN

(75) Inventors: Chong-Sheng Yuan, San Diego, CA (US); Abhijit Datta, Carlsbad, CA (US); Limin Liu, San Diego, CA (US)

(73) Assignee: General Atomics, San Diego, CA (US)

( * ) Notice: Subject to any disclaimer, the term of this patent is extended or adjusted under 35 U.S.C. 154(b) by 344 days.

This patent is subject to a terminal disclaimer.

(21) Appl. No.: 12/120,122

(22) Filed: May 13, 2008

(65) Prior Publication Data

US 2008/0299597 A1 Dec. 4, 2008

Related U.S. Application Data

(63) Continuation-in-part of application No. 11/881,179, filed on Jul. 25, 2007, now Pat. No. 7,855,079.

(60) Provisional application No. 60/833,390, filed on Jul. 25, 2006, provisional application No. 60/858,809, filed on Nov. 13, 2006.

(51) Int. Cl.
*G01N 33/72* (2006.01)
*G01N 33/00* (2006.01)

(52) U.S. Cl. ............... 436/67; 435/2; 435/14; 435/25; 435/381; 436/522; 436/17; 436/66; 436/177

(58) Field of Classification Search ............... 435/2, 14, 435/25, 381, 7.25; 436/17, 66, 67, 177, 522
See application file for complete search history.

(56) References Cited

U.S. PATENT DOCUMENTS

| | | | |
|---|---|---|---|
| 2,713,581 A | 7/1955 | Pannone et al. |
| 4,588,684 A | 5/1986 | Brake |
| 4,837,331 A | 6/1989 | Yamanishi et al. |
| 4,847,195 A | 7/1989 | Khanna et al. |
| 4,948,729 A | 8/1990 | Piatak, Jr. et al. |
| 5,013,647 A | 5/1991 | Town et al. |
| 5,030,563 A | 7/1991 | Schendel et al. |
| 5,120,420 A | 6/1992 | Nankai et al. |

(Continued)

FOREIGN PATENT DOCUMENTS

EP    0 121 352    10/1984

(Continued)

OTHER PUBLICATIONS

Allgrove et al. (1988). Archives of Disease in Childhood 63:418-422.

(Continued)

*Primary Examiner* — Gailene R Gabel
(74) *Attorney, Agent, or Firm* — Morrison & Foerster LLP

(57) ABSTRACT

The invention provides enzymatic methods for direct determination of percentage of glycated hemoglobin in blood samples without the need of a separated measurement of total hemoglobin content in blood samples. The methods utilizes one or two different types of oxidizing agents which selectively oxidize low-molecular weight reducing substances and high-molecular weight (mainly hemoglobin) reducing substances in blood samples, coupled with enzymatic reactions catalyzed by proteases, fructosyl amino acid oxidase. The amount of hydrogen peroxide generated in the reaction is measured for determination of percentage of glycated hemoglobin in blood samples. The invention provides kits for performing the methods of the invention.

12 Claims, 4 Drawing Sheets

U.S. PATENT DOCUMENTS

| | | | |
|---|---|---|---|
| 5,137,821 A | 8/1992 | Sagai et al. |
| 5,171,670 A | 12/1992 | Kronenberg et al. |
| 5,196,314 A | 3/1993 | Town et al. |
| 5,229,286 A | 7/1993 | Jarsch et al. |
| 5,244,796 A | 9/1993 | Levy et al. |
| 5,308,770 A | 5/1994 | Jarsch et al. |
| 5,312,759 A | 5/1994 | Hama et al. |
| 5,320,732 A | 6/1994 | Nankai et al. |
| 5,344,770 A | 9/1994 | Hitomi et al. |
| 5,509,410 A | 4/1996 | Hill et al. |
| 5,628,890 A | 5/1997 | Carter et al. |
| 5,681,529 A | 10/1997 | Taguchi et al. |
| 5,682,884 A | 11/1997 | Hill et al. |
| 5,710,248 A | 1/1998 | Grose |
| 5,712,138 A | 1/1998 | Kato et al. |
| 5,789,221 A | 8/1998 | Kato et al. |
| 5,820,551 A | 10/1998 | Hill et al. |
| 5,824,527 A | 10/1998 | Kato et al. |
| 5,856,104 A | 1/1999 | Chee et al. |
| 5,879,921 A | 3/1999 | Cherry et al. |
| 5,885,811 A | 3/1999 | Hansen |
| 5,914,250 A | 6/1999 | Hansen |
| 5,948,659 A | 9/1999 | Kato et al. |
| 5,948,665 A | 9/1999 | Matsukawa et al. |
| 5,972,294 A | 10/1999 | Smith et al. |
| 5,972,671 A | 10/1999 | Kato et al. |
| 5,972,745 A | 10/1999 | Kalter et al. |
| 5,985,591 A | 11/1999 | Yonehara et al. |
| 6,008,006 A | 12/1999 | Torrens et al. |
| 6,069,297 A | 5/2000 | Luzzatto et al. |
| 6,127,138 A | 10/2000 | Ishimaru et al. |
| 6,127,345 A | 10/2000 | Burnham |
| 6,143,164 A | 11/2000 | Heller et al. |
| 6,194,200 B1 | 2/2001 | Rose et al. |
| 6,270,637 B1 | 8/2001 | Crismore et al. |
| 6,329,161 B1 | 12/2001 | Heller et al. |
| 6,352,835 B1 | 3/2002 | Komori et al. |
| 6,380,380 B1 | 4/2002 | Kaufman |
| 6,451,574 B1 | 9/2002 | Erode, III et al. |
| RE37,919 E | 12/2002 | Kronenberg et al. |
| 6,514,720 B2 | 2/2003 | Komori et al. |
| 6,863,800 B2 | 3/2005 | Karinka et al. |
| 7,153,666 B2 * | 12/2006 | Yuan et al. ............ 435/23 |
| 7,235,378 B2 * | 6/2007 | Yonehara ............ 435/14 |
| 7,276,146 B2 | 10/2007 | Wilsey |
| 7,276,147 B2 | 10/2007 | Wilsey |
| 2002/0009779 A1 | 1/2002 | Meyers et al. |
| 2003/0162242 A1 | 8/2003 | Yonehara |
| 2004/0063213 A1 | 4/2004 | Hirai et al. |
| 2004/0166560 A1 | 8/2004 | Mueller et al. |
| 2004/0171130 A1 | 9/2004 | Yokoi et al. |
| 2005/0014935 A1 | 1/2005 | Yuan et al. |
| 2007/0099283 A1 | 5/2007 | Mueller et al. |
| 2008/0096230 A1 * | 4/2008 | Yuan et al. ............ 435/7.8 |
| 2008/0176296 A1 | 7/2008 | Zelder et al. |
| 2008/0241880 A1 | 10/2008 | Yuan et al. |
| 2008/0299597 A1 | 12/2008 | Yuan et al. |
| 2009/0090623 A1 | 4/2009 | Chuang et al. |
| 2010/0025264 A1 | 2/2010 | Yuan et al. |

FOREIGN PATENT DOCUMENTS

| | | |
|---|---|---|
| EP | 0 127 958 A2 | 12/1984 |
| EP | 0 127 958 A3 | 12/1984 |
| EP | 0 127 958 B1 | 12/1984 |
| EP | 0 127 958 B2 | 12/1984 |
| EP | 0 186 643 | 7/1986 |
| EP | 0 186 643 A1 | 7/1986 |
| EP | 0 189 918 A2 | 8/1986 |
| EP | 0 189 918 A3 | 8/1986 |
| EP | 0 189 918 B1 | 8/1986 |
| EP | 0 196 864 | 10/1986 |
| EP | 0 239 931 | 10/1987 |
| EP | 0 239 931 A1 | 10/1987 |
| EP | 0 351 891 A2 | 1/1990 |
| EP | 0 351 891 A3 | 1/1990 |
| EP | 0 351 891 B1 | 1/1990 |
| EP | 0 821 064 | 1/1998 |
| EP | 1 223 224 | 7/2002 |
| EP | 1 304 385 | 4/2003 |
| EP | 1 542 015 A1 | 6/2005 |
| EP | 1 614 746 A1 | 1/2006 |
| EP | 1 651 759 B1 | 5/2006 |
| GB | 738585 | 10/1955 |
| GB | 1 513 488 | 6/1978 |
| WO | WO-89/03886 | 5/1989 |
| WO | WO-90/12113 | 10/1990 |
| WO | WO-93/06125 | 4/1993 |
| WO | WO-96/28556 | 9/1996 |
| WO | WO-00/28041 | 5/2000 |
| WO | WO-01/47968 | 7/2001 |
| WO | WO-01/68694 | 9/2001 |
| WO | WO-01/90325 | 11/2001 |
| WO | WO-01/90378 | 11/2001 |
| WO | WO-01/98472 | 12/2001 |
| WO | WO-02/20795 | 3/2002 |
| WO | WO-02/064760 | 8/2002 |
| WO | WO-02/072634 | 9/2002 |
| WO | WO-03/042389 | 5/2003 |
| WO | WO-2005/017136 | 2/2005 |
| WO | WO-2007/094354 A1 | 8/2007 |
| WO | WO-2008/013874 A1 | 1/2008 |
| WO | WO-2009/140343 A1 | 11/2009 |

OTHER PUBLICATIONS

Amendment After Final Action (37 C.F.R. Section 1.116) from U.S. Appl. No. 10/622,893, filed Jun. 22, 2006.

Amendment in Response to Non-Final Office Action from U.S. Appl. No. 10/622,893, filed Nov. 22, 2005.

Armbuster. (1987). Fructosamine: Clin. Chem. 33(12):2153-63.

Baker et al. (1991). Clin. Chem. 37(4):552-556.

Bastin et al. (1996). Mol. Biochem. Parasitology 77:235-239.

Baynes et al. eds. (1989). Prog. Clin. Biol. Res. 304:1-410.

Chen et al. (1998). BioTechniques 25(1):22-24.

Communication pursuant to Article 96(2) EPC, from EP Application No. 04 778 420.2-1222, dated Aug. 29, 2006.

Communication under Rule 51(4) EPC, from EP Application No. 04 778 420.2-1222, dated May 31, 2007.

Diazyme Laboratories Division, General Atomics, FAOX-TE Fact Sheet 5 •a. es, (2003).

Entry into the European phase, from EP Application No. 04 778 420.2-1222, filed Feb. 17, 2006.

Final Office Action from U.S. Appl. No. 10/622,893, mailed on Feb. 23, 2006.

Fossati et al. (1980). Clin. Chem. 26(2):227-231.

Frederick et al. (1990). J. Biol. Chem. 265(7):3793-802.

Gerhardinger et al. (1995). The Journal of Biological Chemistry 270(1):218-224.

Hardy et al. (1989). J. Cell. Sci. Suppl. 11:29-43.

Hobom et al. (1995). Dev. Biol. Stand. 11:255-262.

International Preliminary Report on Patentability for PCT/US2004/022908, issued on Jan. 23, 2006, 6 pages.

International Search Report mailed on Jan. 26, 2005, for PCT Patent U.S. Appl. No. PCT/US2004/022908, 5 pages.

International Search Report mailed on Nov. 20, 2007, for PCT Application No. PCT/US2007/016774, filed Jul. 25, 2007, 2 pages.

Invitrogen Catalogue. (2002). "pBAD TOPO TA Expression Kit," p. 75.

Kouzuma et al. (2002). Clin. Chimi, Acta. 324:61-71.

Kuhn et al. (1979). Mol. Gen. Genet. 167(3):235-241.

Luo, Y-C. et al. (2006, e-pub Sep. 5, 2006). "An Amperometric Uric Acid Biosensor Based on Modified Ir-C Electrode," *Biosensors and Bioelectronics* 22:482-488.

Michiels et al. (2001). Trends Microbiol. 9(4):164-168.

Nagelkerken et al. (1997). Electrophoresis 18:2694-98.

Non-Final Office Action from U.S. Appl. No. 10/622,893, mailed on Jul. 22, 2005.

Notice of Allowance and Examiner's Amendment from U.S. Appl. No. 10/622,893, mailed on Aug. 10, 2006.

Olah et al. (1994). Biochem. 221:94-102.

Peakman et al. (1992). Nucleic Acids Res. 20(22):6111-12.

Phillipou et al. (1988). Clin. Chem. 34(8):1561-64.

Prickett et al. (1989). BioTechniques 796):580-584.
Response to Office Action, from EP Application No. 04 778 420.2-1222, filed Mar. 7, 2007.
Response to Restriction Requirement from U.S. Appl. No. 10/622,893, filed on May 16, 2005.
Restriction Requirement from U.S. Appl. No. 10/622,893, mailed on Apr. 14, 2005.
Roesser et al. (1991). Nucleic Acids Res. 19(4):795-800.
Rudiger et al. (1997). BioTechniques 23(1):96-97.
Saier et al. (1988). FASEB J. 2(3):199-208.
Sakai et al. (1995). Biosci. Biotech. Biochem. 59(3):487-491.
Sakurabayashi et al. (2003). "New Enzymatic Assay for Glycohemoglobin," Clinical Chemistry 49(2):269-274.
Schleicher et al. (1988). Clin. Chem. 34(2):320-323.
Sigma-Aldrich Catalog No. 82452, printed in Mar. 2, 2004, 1 page.
Takahashi et al. (1997). J. Biol. Chem. 272(19):12505-7.
Takahashi et al. (1997). J. Biol. Chem. 272(6):3437-43.
Tolbert et al. (1998). J. Neurochem. 70:113-119.
Tsenq et al. (1996). Gene 169:287-288.
U.S. Appl. No. 11/595,209, filed Nov. 8, 2006, by Yuan et al.
Unknown. (1972). Biochemistry 11(9):1726-32.
Wang et al. (1996). Gene 169(1):53-58.
Wang, J. (2008, e-pub Dec. 23, 2007). "Electrochemical Glucose Biosensors," *Chem. Rev.* 108(2):814-825.
Watson et al. (1987). *Molecular Biology of the Gene, 4th Edition*. The Bejacmin/Cummings Pub. Co., p. 224.
Written Opinion mailed on Nov. 20, 2007, for PCT Application No. PCT/US2007/016774, filed Jul. 25, 2007, 6 pages.
Worthington Catalog, Proteinase K, located at <http://worthington-biochem.com/PROK.html>, printed on Mar. 2, 2004, 4 pages.
Xie et al. (1998). Endocrinology 139(11):4563-67.
Yoshida et al. (1995). Applied and Environmental Microbiology 61(12):4487-4489.
Yoshida et al. (1996). European Journal of Biochemistry 242(3):499-505.
Amendment in Response to Non-Final Office Action submitted on Feb. 19, 2010, for U.S. Appl. No. 11/881,179, filed Jul. 25, 2007, 16 pages.
Amendment in Response to Non-Final Office Action submitted on Jul. 19, 2010, for U.S. Appl. No. 11/881,179, filed Jul. 25, 2007, 10 pages.
Branden, C. et al. (1991). "Prediction, Engineering, and Design of Protein Structures," in Chapter 16 in *Introduction to Protein Structure*, Garland Publishing Inc.: New York, NY, pp. 247.
Fang, L. et al. (Feb. 22, 2008, e-pub. Sep. 9, 2007). "An Electrochemical Biosensor of the Ketone 3-β-hydroxybutyrate for Potential Diabetic Patient Management," *Sensors and Actuators B: Chemical* 129(2):818-825.

FREEDICTIONARY.COM (Date Unknown). "Glycosylated Hemoglobin," located at <http://medical-dictionary.thefreedictionary.com/Hba1c>, last visited on Nov. 4, 2010, 3 pages.
International Search Report mailed on Nov. 4, 2009, for PCT Patent Application No. PCT/US2009/043725, 2 pages.
Nagata, R. et al. (1995). "A Glucose Sensor Fabricated by the Screen Printing Technique," *Biosens. Bioelectron.* 10(3-4):261-267.
Non-Final Office Action mailed on May 15, 2009, for U.S. Appl. No. 11/595,209, filed Nov. 8, 2006, 12 pages.
Non-Final Office Action mailed on May 27, 2010, or U.S. Appl. No. 11/881,179, filed Jul. 25, 2007, 13 pages.
Notice of Allowance mailed on Aug. 11, 2010, for U.S. Appl. No. 11/881,179, filed Jul. 25, 2007, 4 pages.
Restriction Requirement mailed on Jun. 12, 2009, for U.S. Appl. No. 11/881,179, filed Jul. 25, 2007, 7 pages.
Response to Restriction Requirement submitted on Jul. 10, 2009, for U.S. Appl. No. 11/881,179, filed Jul. 25, 2007, 7 pages.
Rosen-Margalit, I. et al. (1993). "Novel Approaches for the Use of Mediators in Enzyme Electrodes," *Biosens. Bioelectron.* 8(6):315-323.
Sakaguchi, A. et al. (Jun. 1, 2003). "Development of Highly-Sensitive Fructosyl-Valine Enzyme Sensor Employing Recombinant Fructosyl Amine Oxidase," *Electrochemisty* 71(6):442-445.
Seffernick, J.L. et al. (Apr. 2001). "Melamine Deaminase and Atrazine Chlorohydrolase: 98 Percent Identical but Functionally Different," *J. Bacteriol.* 183(8):2405-2410.
Shaklai, N. et al. (Mar. 25, 1984). "Noenzymatic Glycosylation of Human Serum Albumin Alters Its Conformation and Function," *The Journal of Biological Chemistry* 259(6):3812-3817.
Tsugawa, W. et al. (Dec. 1, 2001). "Fructosyl Amine Sensing Based on Prussian Blue Modified Enzyme Electrode," *Electrochemistry* 69(12):973-975.
Wang, J. et al. (Nov. 1, 1994). "Highly Selective Membrane-Free, Mediator-Free Glucose Biosensor," *Anal. Chem.* 66(21):3600-3603.
Witkowski, A. et al. (1999, e-pub. Aug. 18, 1999). "Conversion of a β-Ketoacyl Snythase to a Malonyl Decarboxylase by Replacement of the Active-Site Cysteine with Glutamine," *Biochemistry* 38(36):11643-11650.
Written Opinion of the International Searching Authority mailed on Jan. 23, 2006, for PCT Patent Application No. PCT/US2004/022908, filed on Jul. 16, 2004, 5 pages.
Written Opinion of the International Searching Authority mailed on Nov. 4, 2009, for PCT Patent Application No. PCT/US2009/043725, 6 pages.
Wu, X. (2000, e-pub. Jan. 19, 2000). "Cloning of Amadoriase I Isoenzyme from *Aspergillus* sp.: Evidence of FAD Covalently Linked to Cys342," *Biochemistry* 39(6):1515-1521.
Wu, X. et al. (2003). "Enzymatic Deglycation of Proteins," *Archives of Biochemistry and Biophysics* 419:16-24.

* cited by examiner

METHODS FOR ASSAYING PERCENTAGE OF GLYCATED HEMOGLOBIN

CROSS-REFERENCES TO RELATED APPLICATIONS

This application is a continuation-in-part application of U.S. Ser. No. 11/881,179, filed Jul. 25, 2007, now U.S. Pat. No. 7,855,079, which claims the priority benefit of provisional patent applications U.S. Ser. Nos. 60/833,390, filed Jul. 25, 2006, and 60/858,809, filed Nov. 13, 2006, all of which are incorporated herein in their entirety by reference.

STATEMENT REGARDING FEDERALLY SPONSORED RESEARCH OR DEVELOPMENT

Not applicable.

FIELD OF THE INVENTION

The invention provides direct enzymatic assay for determining percentage of glycated hemoglobin in a blood sample.

BACKGROUND OF THE INVENTION

A glycated protein is a substance which is produced by the non-enzymatic and irreversible binding of the amino group of an amino acid constituting a protein, with the aldehyde group of a reducing sugar such as aldose. See e.g., U.S. Pat. No. 6,127,138. Such a non-enzymatic and irreversible binding reaction is also called "Amadori rearrangement," and therefore the above-mentioned glycated protein may also be called "Amadori compound" in some cases.

Nonenzymatic glycation of proteins has been implicated in the development of certain diseases, e.g., diabetic complications and the aging process (Takahashi et al., *J. Biol. Chem.*, 272(19):12505-7 (1997); and Baynes and Monnier, *Prog. Clin. Biol. Res.*, 304:1-410 (1989)). This reaction leads to dysfunction of target molecules through formation of sugar adducts and cross-links. Considerable interest has focused on the Amadori product that is the most important "early" modification during nonenzymatic glycation in vitro and in vivo.

Various assays for glycated proteins are known. For example, U.S. Pat. No. 6,127,138 discloses that a sample containing a glycated protein is treated with Protease XIV or a protease from *Aspergillus* genus, thereafter (or while treating the sample with the above protease) FAOD (fructosyl amino acid oxidase) is caused to react with the sample so as to measure the amount of oxygen consumed by the FAOD reaction or the amount of the resultant reaction product, thereby to measure the glycated protein.

In another example, U.S. Pat. No. 6,008,006 discloses that the amount of glycated proteins in a sample can be quantified by reacting the sample with first a reagent which is a combination of a protease and a peroxidase and second with a ketoamine oxidase. U.S. Pat. No. 6,008,006 also discloses a kit which contains the combined peroxidase/protease enzyme reagent and also the ketoamine oxidase. U.S. Pub. No. 2005/0014935 also discloses methods and kits for measuring amount of glycated protein using a chimeric amadoriase. U.S. Pub. No. 2003/0162242 and EP 1304385 A1 also disclose methods of selectively determining glycated hemoglobin.

Previously described methods for determining percentage of glycated hemoglobin A1c require a separate measurement of total hemoglobin in the samples. When a chemistry analyzer is used to determine the value of percentage of glycated hemoglobin A1c, a dual channel format is required. In this format, two separate assays are performed to determine 1) glycated hemoglobin A1c concentration, and 2) total hemoglobin concentration in the samples; and followed by calculating the ratio of glycated HbA1c to total hemoglobin to obtain percentage of HbA1c.

All patents, patent applications, and publications cited herein are hereby incorporated by reference in their entirety.

SUMMARY OF THE INVENTION

The invention provides methods for direct determination of percentage of glycated hemoglobin in a blood sample without the need of a separated measurement of total hemoglobin in the sample. Since there is no need for a separate measurement of total hemoglobin and no need for a ratio calculation step, the present methods can be fully automated and used with various chemical analyzers in a single channel format.

In one aspect, the present invention provides methods for directly assaying percentage of total glycated hemoglobin or percentage of glycated hemoglobin A1c in a blood sample without measuring the total hemoglobin in the blood sample in a separate process, said method comprising: a) contacting protein fragments containing glycated peptides or glycated amino acids with a fructosyl amino acid oxidase to generate hydrogen peroxide ($H_2O_2$), wherein the protein fragments are generated by contacting the blood sample with 1) a lysing buffer which releases hemoglobin from red blood cells in the blood sample; 2) a first oxidizing agent which selectively oxidizes low molecular weight reducing substances; 3) a second oxidizing agent which selectively oxidizes high molecular weight reducing substances, and 4) a protease which digests glycated hemoglobin into glycated peptides or glycated amino acids; b) measuring the amount of $H_2O_2$ generated in step a); and c) determining percentage of total glycated hemoglobin or percentage of glycated hemoglobin A1c in the sample by applying a signal measured in step b) based on the amount of $H_2O_2$ to a calibration curve without measuring the total hemoglobin in the blood sample separately. In some embodiments, the amount of $H_2O_2$ generated step a) is measured by an electrochemical biosensor. In some embodiments, the amount of $H_2O_2$ generated in step a) is measured by contacting said $H_2O_2$ with a color forming substance in the presence of a peroxidase to generate a measurable signal.

In some embodiments, the first oxidizing agent is Dess-Martin periodinane or N-ethylmaleimide, and wherein the second oxidizing agent is a tetrazolium salt.

In some embodiments, the lysing buffer contains the first oxidizing agent and/or the second oxidizing agent. In some embodiments, the lysing buffer contains the first oxidizing agent, the second oxidizing agent, and the protease. In some embodiments, the lysing buffer contains the protease.

In some embodiments, the first oxidizing agent and the second oxidizing agent are formulated in a single composition. In some embodiments, the first oxidizing agent and the second oxidizing agent are formulated in a separate composition. In some embodiments, the protease is formulated in a single composition with the first oxidizing agent or the second oxidizing agent. In some embodiments, the first oxidizing agent, the second oxidizing agent, and the protease are formulated in a single composition. In some embodiments, the fructosyl amino acid oxidase, the peroxidase, and the color forming substance are formulated in a single composition.

In another aspect, the invention provides methods for directly assaying percentage of total glycated hemoglobin or percentage of glycated hemoglobin A1c in a blood sample without measuring the total hemoglobin in the blood sample in a separate process, said method comprising: a) contacting protein fragments containing glycated peptides or glycated amino acids with a fructosyl amino acid oxidase to generate hydrogen peroxide ($H_2O_2$), wherein the protein fragments are generated by contacting the blood sample with 1) a lysing buffer which releases hemoglobin from red blood cells in the blood sample; 2) an oxidizing agent which is a tetrazolium salt, and 3) a protease which digests glycated hemoglobin into glycated peptides or glycated amino acids; b) measuring the amount of $H_2O_2$ generated in step a); and c) determining percentage of total glycated hemoglobin or percentage of glycated hemoglobin A1c in the sample by applying a signal measured in step b) based on the amount of $H_2O_2$ to a calibration curve without measuring the total hemoglobin in the blood sample separately. In some embodiments, the amount of $H_2O_2$ generated step a) is measured by an electrochemical biosensor. In some embodiments, the amount of $H_2O_2$ generated in step a) is measured by contacting said $H_2O_2$ with a color forming substance in the presence of a peroxidase to generate a measurable signal.

In some embodiments, the lysing buffer contains the oxidizing agent. In some embodiments, the lysing buffer contains the protease. In some embodiments, the oxidizing agent and the protease are formulated in a single composition.

In some embodiments, tetrazolium salt is 2-(4-iodophenyl)-3-(2,4-dinitrophenyl)-5-(2,4-disulfophenyl)-2H-tetrazolium monosodium salt or 2-(4-iodophenyl)-3-(4-nitrophenyl)-5-(2,4-disulfophenyl)-2H-tetrazolium monosodium salt.

In some embodiments, the color forming substance is N-Carboxymethylaminocarbonyl)-4,4'-bis(dimethylamino)-diphenylamine sodium salt (DA-64), N,N,N'N',N'',N''-Hexa (3-sulfopropyl)-4,4',4''-triamino-triphenylmethane hexasodium salt (TPM-PS), or 10-(carboxymethylaminocarbonyl)-3,7-bis(dimethylamino)-phenothiazine sodium salt (DA-67).

In some embodiments, the blood sample is a whole blood or collected blood cells.

In some embodiments, the protease is an endo-type protease or an exo-type protease. In some embodiments, the protease is selected from the group consisting of proteinase K, pronase E, ananine, thermolysin, subtilisin and cow pancreas proteases. In some embodiments, the protease is a neutral protease of *Aspergillus* or *Bacillus* origin. In some embodiments, the protease generates a glycated peptide from about 2 to about 30 amino acid residues. In some embodiments, the protease generates glycated glycine, glycated valine or glycated lysine residue or a glycated peptide comprising glycated glycine, glycated valine or glycated lysine residue.

In some embodiments, the peroxidase is horseradish peroxidase.

In some embodiments, the protein fragments containing the glycated peptide or glycated amino acid are contacted with the fructosyl amino acid oxidase and the peroxidase sequentially or simultaneously.

In some embodiments, the fructosyl amino acid oxidase comprises the amino acid sequence set forth in

SEQ ID NO: 1
(MGGSGDDDDLALAVTKSSSLLIVGAGTWGTSTALHLARRGYTNVTVLDP

YPVPSAISAGNDVNKVISSGQYSNNKDEIEVNEILAEEAFNGWKNDPLFK

PYYHDTGLLMSACSQEGLDRLGVRVRPGEDPNLVELTRPEQFRKLAPEGV

-continued
LQGDFPGWKGYFARSGAGWAHARNALVAAAREAQRMGVKFVTGTPQGRVV

TLIFENNDVKGAVTGDGKIWRAERTFLCAGASAGQFLDFKNQLRPTAWTL

VHIALKPEERALYKNIPVIFNIERGFFFEPDEERGEIKICDEHPGYTNMV

QSADGTMMSIPFEKTQIPKEAETRVRALLKETMPQLADRPFSFARICWCA

DTANREFLIDRHPQYHSLVLGCGASGRGFKYLPSIGNLIVDAMEGKVPQK

IHELIKWNPDIAANRNWRDTLGRFGGPNRVMDFHDVKEWTNVQYRDISKL

KGELEGLPIPNPLLRTGHHHHHH).

In some embodiments, the method is used in the prognosis or diagnosis of a disease or disorder. In some embodiments, the disease or disorder is diabetes.

In another aspect, the invention provides kits for directly assaying percentage of total glycated hemoglobin or percentage of glycated hemoglobin A1c in a blood sample without the need of a separate measurement of total hemoglobin content in blood samples, comprising: a) a lysing buffer that lyses blood cells to release hemoglobin; b) a first oxidizing agent that selectively oxidizes low molecular weight reducing substances; c) a second oxidizing agent that selectively oxidizes high molecular weight reducing substances; d) a protease that hydrolyzes hemoglobin into protein fragments containing glycated peptides or glycated amino acids; e) a fructosyl amino acid oxidase that reacts with glycated peptides and glycated amino acids to generate hydrogen peroxide ($H_2O_2$); f) a peroxidase and a color forming substance or an electrochemical biosensor for measuring the amount of $H_2O_2$; and g) calibrator(s) with known percentage of glycated hemoglobin or known percentage of glycated hemoglobin A1c for use in constructing a calibration curve. The kit may further comprise instructions to perform the methods described herein.

In some embodiments, the first oxidizing agent and/or the second oxidizing agent are contained in the lysing buffer. In some embodiments, the first oxidizing agent and/or the second oxidizing agent are contained in the same buffer with the protease.

In another aspect, the invention provides kits for directly assaying percentage of total glycated hemoglobin or percentage of glycated hemoglobin A1c in a blood sample without the need of a separated measurement of total hemoglobin content in blood samples, said kit comprising: a) a lysing buffer that lyses blood cells to release hemoglobin; b) an oxidizing agent, wherein the oxidizing agent is a tetrazolium salt; c) a protease that hydrolyzes hemoglobin into protein fragments containing glycated peptides or glycated amino acids; d) a fructosyl amino acid oxidase that reacts with glycated peptides and glycated amino acids to generate hydrogen peroxide ($H_2O_2$); e) a peroxidase and a color forming substance or an electrochemical biosensor for measuring the amount of $H_2O_2$; and f) calibrator(s) with known percentage of glycated hemoglobin or known percentage of glycated hemoglobin A1c for use in constructing a calibration curve. The kit may further comprise instructions to perform the methods described herein.

In some embodiments, the oxidizing agent is contained in the lysing buffer. In some embodiments, the protease is contained in the lysing buffer. In some embodiments, the oxidizing agent and the protease are formulated in a single composition.

BRIEF DESCRIPTION OF THE SEVERAL VIEWS OF THE DRAWING(S)

DETAILED DESCRIPTION OF THE INVENTION

Figure 1:
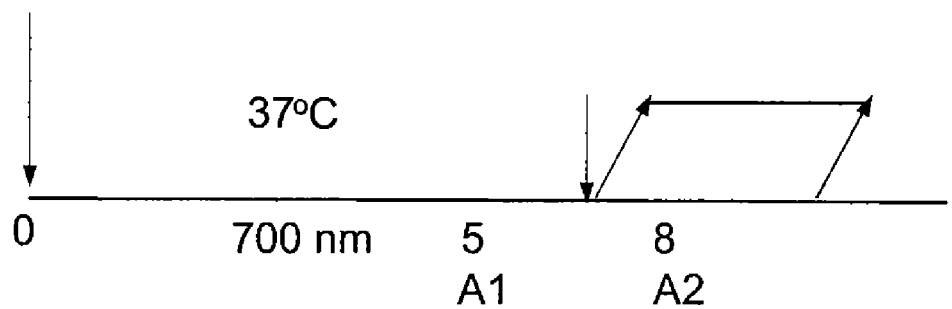
FIG. 1 shows the timeline of the single channel HbA1c enzymatic assay procedure.

The invention provides enzymatic methods for direct determination of percentage of glycated hemoglobin in blood samples without the need of a separate measurement of total hemoglobin content in blood samples. In one aspect, the methods utilizes two different types of oxidizing agents which selectively oxidize low-molecular weight reducing substances (mainly ascorbic acid and free thio-containing molecules) and high-molecular weight reducing substances (mainly hemoglobin) in blood samples, coupled with enzymatic reactions catalyzed by proteases, fructosyl amino acid oxidase, and peroxidase. In another aspect, the methods utilizes one type of oxidizing agent which selectively oxidize high-molecular weight reducing substances in blood samples, coupled with enzymatic reactions catalyzed by proteases, fructosyl amino acid oxidase, and peroxidase. The invention also provides kits for performing the methods of the invention.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, a "fructosyl amino acid oxidase" or (FAOD) refers to an enzyme catalyzing the oxidative deglycation of Amadori products to yield corresponding amino acids, glucosone, and $H_2O_2$, as shown in the following reaction:

$R_1$—CO—$CH_2$—NH—$R_2$+$O_2$+$H_2O$→$R_1$—CO—CHO+$R_2$—$NH_2$+$H_2O_2$ wherein $R_1$ represents the aldose residue of a reducing sugar and $R_2$ represents a residue of an amino acid, protein or peptide. Other synonyms of amadoriase include amadoriase, fructosyl amine:oxygen oxidoreductase (FAOO), and fructosyl valine oxidase (FVO). For purposes herein, the name "fructosyl amino acid oxidase" is used herein, although all such chemical synonyms are contemplated. "Fructosyl amino acid oxidase" also encompasses a functional fragment or a derivative that still substantially retain its enzymatic activity catalyzing the oxidative deglycation of Amadori products to yield corresponding amino acids, glucosone, and $H_2O_2$. Typically, a functional fragment or derivative retains at least 50% of its amadoriase activity. Preferably, a functional fragment or derivative retains at least 60%, 70%, 80%, 90%, 95%, 99% or 100% of its amadoriase activity. It is also intended that a fructosyl amino acid oxidase can include conservative amino acid substitutions that do not substantially alter its activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., *Molecular Biology of the Gene*, 4th Edition, 1987, The Benjamin/Cummings Pub. Co., p. 224). Such exemplary substitutions are preferably made in accordance with those set forth in TABLE 1 as follows:

TABLE 1

| Original residue | Conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions.

As used herein, "peroxidase" refers to an enzyme that catalyses a host of reactions in which hydrogen peroxide is a specific oxidizing agent and a wide range of substrates act as electron donors. It is intended to encompass a peroxidase with conservative amino acid substitutions that do not substantially alter its activity. The chief commercially available peroxidase is horseradish peroxidase.

As used herein, a "composition" refers to any mixture of two or more products or compounds. It may be a solution, a suspension, a liquid, a powder, a paste, aqueous, non-aqueous, or any combination thereof.

B. Methods of Directly Assaying Percentage of Glycated Hemoglobin

In one aspect, the present invention provides methods for directly assaying percentage of total glycated hemoglobin or percentage of glycated hemoglobin A1c in a blood sample without measuring the total hemoglobin in the blood sample in a separate process, said method comprising: a) contacting protein fragments containing glycated peptides or glycated amino acids with a fructosyl amino acid oxidase to generate hydrogen peroxide ($H_2O_2$), wherein the protein fragments are generated by contacting the blood sample with 1) a lysing buffer which releases hemoglobin from red blood cells in the blood sample; 2) a first oxidizing agent which selectively oxidizes low molecular weight reducing substances; 3) a second oxidizing agent which selectively oxidizes high molecular weight reducing substances, and 4) a protease which digests glycated hemoglobin into glycated peptides or glycated amino acids; b) measuring the amount of $H_2O_2$ generated in step a); and c) determining percentage of total glycated hemoglobin or percentage of glycated hemoglobin A1c in the sample by applying a signal measured in step b) based on the amount of $H_2O_2$ to a calibration curve without measuring the total hemoglobin in the blood sample separately.

In another aspect, the present invention is directed to a method for directly assaying percentage of total glycated hemoglobin or percentage of glycated hemoglobin A1c, said method comprising: a) lysing red blood cells in a blood sample with a lysing buffer to release hemoglobin; b) oxidizing the lysate with a first oxidizing agent which selectively oxidizes low molecular weight reducing substances; c) oxidizing the lysate with a second oxidizing agent which selectively oxidizes high molecular weight reducing substances; d) contacting the lysate with a protease to form protein fragments containing glycated peptides and/or glycated amino acids; e) contacting the protein fragments with a fructosyl amino acid oxidase to generate hydrogen peroxide ($H_2O_2$); f) allowing oxidization of a color forming substance by $H_2O_2$ generated in step e) in the presence of a peroxidase under Trinder reaction and by unreacted second oxidizing agent to generate a measurable signal; and g) assessing the signal generated in step f); and h) determining the percentage of total glycated hemoglobin or percentage of glycated hemoglobin A1c in the sample by comparing the signal to a calibration curve without measuring the total hemoglobin in the blood sample separately.

In another aspect, the invention provides a method for directly assaying percentage of total glycated hemoglobin or percentage of glycated hemoglobin A1c without measuring total hemoglobin separately in a blood sample, said method comprising: a) lysing red blood cells in a blood sample with a lysing buffer to release hemoglobin; b) oxidizing the lysate with a first oxidizing agent, wherein the first oxidizing agent is Dess-Martin periodinane and/or N-ethylmaleimide; c) oxidizing the lysate with a second oxidizing agent, wherein the second oxidizing agent is a tetrazolium salt; d) contacting the lysate with a protease to form protein fragments containing glycated peptides and/or glycated amino acids; e) contacting the protein fragments with a fructosyl amino acid oxidase to generate hydrogen peroxide ($H_2O_2$); f) allowing oxidization of a color forming substance by $H_2O_2$ generated in step e) in the presence of a peroxidase under Trinder reaction to generate a measurable signal; g) assessing the signal generated in step f); and h) determining the percentage of total glycated hemoglobin or percentage of glycated hemoglobin A1c in the sample by comparing the signal to a calibration curve without measuring the total hemoglobin in the blood sample separately.

The blood sample may be lysed, oxidized by the first oxidizing agent, oxidized by the second oxidizing agent, and the lysate fragmented by the protease simultaneously or by separate steps. Any combination of two or more of steps may be performed simultaneously. In some embodiments, steps involving lysing the red blood cells in the sample and oxidizing by the first oxidizing agent, lysing the red blood cells and oxidizing by the second oxidizing agent, oxidizing with the first oxidizing agent and the second oxidizing agent, or lysing the red blood cells and oxidizing with the first oxidizing agent and the second oxidizing agent are performed simultaneously. In some embodiments, steps involving lysing the red blood cells and fragmenting the lysate by the protease, oxidizing with the first oxidizing agent and fragmenting the lysate by the protease, oxidizing with the second oxidizing agent and fragmenting the lysate by the protease, or oxidizing with the first oxidizing agent and the second oxidizing agent and fragmenting the lysate by the protease are performed simultaneously. In some embodiments, the steps involving lysing the red blood cells, oxidizing with the first oxidizing agent and the second oxidizing agent, and fragmenting the lysate are performed simultaneously. In some embodiments, the first oxidizing agent and/or the second oxidizing agent are contained in the lysis buffer, or added into the blood sample at the same time that the lysis buffer is added. In some embodiments, the protease is also included in the lysis buffer with the first and the second oxidizing agent or added into the blood sample at the same time that the lysis buffer and the first and the second oxidizing agents are added into the blood sample. In some embodiments, the first and/or the second oxidizing agent are in the same solution with the protease solution before adding into the red blood cell lysate. In some embodiments, the first oxidizing agent and lysing buffer are formulated in a single composition. In some embodiments, the protease and the first oxidizing agent or the second oxidizing agent are formulated in a single composition. In some embodiments, the first and the second oxidizing agents are formulated in a single composition. In some embodiments, the first and the second oxidizing agents are formulated in a separate composition. In some embodiments, the lysis buffer contains the protease, or the protease is added into the blood sample at the same time that the lysis buffer is added.

The first oxidizing agent is a type of oxidizing agent that selectively oxidizes low molecular weight (M.W.<3000) reducing substances. The first oxidizing agent has higher oxidizing power toward low molecular weight reducing substances than high molecular weight (M.W.>3000) reducing substances. Examples of low molecular weight substances in the blood sample are ascorbic acid and free thio containing molecules. Examples of first oxidizing agent are Dess-Martin periodinane and N-ethyl maleimide. Other examples of first oxidizing agents are sodium iodoacetate, sodium periodate, and Chloramine-T. In some embodiments, more than one first oxidizing agents (e.g., both Dess-Martin periodinane and N-ethyl maleimide) are used.

The second oxidizing agent is a type of oxidizing agent that selectively oxidizes high molecular weight (M.W.>3000) reducing substances. The second oxidizing agent has higher oxidizing power toward high molecular weight reducing substances than low molecular weight reducing substance. An example of high molecular weight substances in the blood sample is hemoglobin. An example of second oxidizing agent is a tetrazolium salt (e.g., 2-(4-iodophenyl)-3-(2,4-dinitrophenyl)-5-(2,4-disulfophenyl)-2H-tetrazolium monosodium salt, or 2-(4-iodophenyl)-3-(4-nitrophenyl)-5-(2,4-disulfophenyl)-2H-tetrazolium monosodium salt). Other examples of second oxidizing agent are sodium dodecyl sulfate, potassium ferricyanide (III), and potassium iodate. In some embodiments, more than one second oxidizing agent is used.

In another aspect, the invention provides methods for directly assaying percentage of total glycated hemoglobin or percentage of glycated hemoglobin A1c in a blood sample without measuring the total hemoglobin in the blood sample in a separate process, said method comprising: a) contacting protein fragments containing glycated peptides or glycated amino acids with a fructosyl amino acid oxidase to generate hydrogen peroxide ($H_2O_2$), wherein the protein fragments are generated by contacting the blood sample with 1) a lysing buffer which releases hemoglobin from red blood cells in the blood sample; 2) an oxidizing agent which is a tetrazolium salt, and 3) a protease which digests glycated hemoglobin into glycated peptides or glycated amino acids; b) contacting $H_2O_2$ generated in step a) with a color forming substance in the presence of a peroxidase to generate a measurable signal; and c) determining percentage of total glycated hemoglobin or percentage of glycated hemoglobin A1c in the sample by applying the signal generated in step b) to a calibration curve without measuring the total hemoglobin in the blood sample separately. Any tetrazolium salt described herein may be used. Steps a) and b) may be performed sequentially or simultaneously. In some embodiments, the lysing buffer contains the oxidizing agent. In some embodiments, the lysing buffer contains the protease. In some embodiments, the lysing buffer contains the oxidizing agent and the protease. In some embodiments, the oxidizing agent and the protease are formulated in a single composition.

Blood samples that can be assayed using the present methods include whole blood or collected blood cells. The red blood cells in the blood sample are lysed in a lysing buffer to release hemoglobin. Any lysing buffer (e.g., in the acidic or alkaline pH ranges) that can lyse the red blood cells and release the hemoglobin can be used. Lysing buffer generally contains a detergent, such as Triton (e.g., Triton X-100), Tween (e.g., Tween 20), sodium dodecyl sulfate (SDS), cetyltrimethylammonium bromide (CTAB), tetradecyltrimethylammonium bromide (TTAB), polyoxyethylene lauryl ethers (POEs), and Nonidet P-40 (NP-40).

Any suitable protease can be used in the present methods. Either an endo-type protease or an exo-type protease can be used. Exemplary endo-type proteases include trypsin, α-chymotrypsin, subtilisin, proteinase K, papain, cathepsin B, pepsin, thermolysin, protease XVII, protease XXI, lysyl-endopeptidase, proleacher and bromelain F. Exemplary exo-type proteases include an aminopeptidase or a carboxypeptidase. In one example, the protease is proteinase K, pronase E, ananine, thermolysin, subtilisin or cow pancreas proteases. Metaloproteases and neutral proteinases from Aspergillus sps, Alicyclobacillus sps, and Bacillus sps may also be used.

The protease can be used to generate a glycated peptide of any suitable size. For example, the protease can be used to generate a glycated peptide from about 2 to about 30 amino acid residues. In another example, the protease is used to generate glycated glycine, glycated valine or glycated lysine residue or a glycated peptide comprising glycated glycine, glycated valine or glycated lysine residue.

Glycated peptide and/or glycated amino acid are contacted with a fructosyl amino acid oxidase. Any fructosyl amino acid oxidase (FAOD) can be used. Fructosyl amino acid oxidase may be purified or recombinantly produced. Any naturally occurring species may be used. In one example, the FAOD used is of Aspergillus sp. origin (See, e.g., Takahashi et al., J. Biol. Chem. 272(6):3437-43, 1997). Other fructosyl amino acid oxidase, e.g., disclosed in GenBank Accession No. U82830 (Takahashi et al., J. Biol. Chem., 272(19):12505-12507 (1997) and disclosed U.S. Pat. No. 6,127,138 can also be used. A functional fragment or a derivative of an amadoriase that still substantially retain its enzymatic activity catalyzing the oxidative deglycation of Amadori products to yield corresponding amino acids, glucosone, and $H_2O_2$ can also be used.

Normally, a functional fragment or a derivative of an amadoriase retains at least 50% of its enzymatic activity. Preferably, a functional fragment or a derivative of an amadoriase retain at least 50%, 60%, 70%, 80%, 90%, 95%, 99% or 100% of its enzymatic activity.

Any of the chimeric proteins having the enzymatic activities of FAOD described in the U.S. Pub. No. 2005/0014935 can be used. In some embodiments, the fructosyl amino acid oxidase comprises from the N-terminus to C-terminus: a) a first peptidyl fragment comprising a bacterial leader sequence from about 5 to about 30 amino acid residues; and b) a second peptidyl fragment comprising an FAOD. In some embodiments, the FAOD comprises the following amino acid sequence:

(SEQ ID NO: 1)
MGGSGDDDDLALAVTKSSSLLIVGAGTWGTSTALHLARRGYTNVTVLDPY

PVPSAISAGNDVNKVISSGQYSNNKDEIEVNEILAEEAFNGWKNDPLFKP

YYHDTGLLMSACSQEGLDRLGVRVRPGEDPNLVELTRPEQFRKLAPEGVL

QGDFPGWKGYFARSGAGWAHARNALVAAAREAQRMGVKFVTGTPQGRVVT

LIFENNDVKGAVTGDGKIWRAERTFLCAGASAGQFLDFKNQLRPTAWTLV

HIALKPEERALYKNIPVIFNIERGFFFEPDEERGEIKICDEHPGYTNMVQ

SADGTMMSIPFEKTQIPKEAETRVRALLKETMPQLADRPFSFARICWCAD

TANREFLIDRHPQYHSLVLGCGASGRGFKYLPSIGNLIVDAMEGKVPQKI

HELIKWNPDIAANRNWRDTLGRFGGPNRVMDFHDVKEWTNVQYRDISKLK

GELEGLPIPNPLLRTGHHHHHH.

The chimeric protein may be produced in bacterial cells, such as E. coli. The protein produced may be purified and assayed for the enzymatic activities. Assays for enzymatic activities of FAOD are known in the art (See e.g., Takahashi et al., J. Biol. Chem., 272(6):3437-43 (1997) and U.S. Pat. No. 6,127,138). Four exemplary assays for enzymatic activities of amadoriases are disclosed in Takahashi et al., J. Biol. Chem., 272(6):3437-43 (1997).

The hydrogen peroxide generated in the reaction catalyzed by the fructosyl amino acid oxidase is assessed by any known methods, such as by an electrochemical biosensor or by Trinder reaction. Any known electrochemical biosensors that measure the amount of hydrogen peroxide may be used. See Wang et al., Chem. Rev. 108:814-825, 2008; Luo et al., Biosensors and Bioelectronics 22:482-488, 2006; U.S. Pat. Nos. 5,628,890; 5,682,884; 5,120,420; 6,999,810; and 6,587,705.

To use Trinder reaction, a color forming substance and a peroxidase is added into the reaction, the color forming substance is oxidized by the hydrogen peroxide to form a color substance such as quinoneimine or Bindschedler's green derivatives and $H_2O$. The amount of quinoneimine or Bindschedler's green product generated can be determined by measuring absorbance between about 500 nm to about 800 nm (such as around 700 nm). Without wishing to be bound by theory, the second oxidizing agent unreacted with the high molecular weight substance in the blood lysate may also react with the color forming substance to the form colored product, and thus the absorbance measured reflects the percentage of total glycated hemoglobin and percentage of glycated hemoglobin A1c in the blood sample. Examples of color forming substances are N-(Carboxymethylaminocarbonyl)-4,4'-bis (dimethylamino)-diphenylamine sodium salt (DA-64), N,N,N'N',N'',N'''-Hexa(3-sulfopropyl)-4,4',4''-triamino-triphenyl-methane hexasodium salt (TPM-PS), and 10-(carboxymethylaminocarbonyl)-3,7-bis(dimethylamino)- phenothiazine sodium salt (DA-67). An example of peroxidase is a horseradish peroxidase.

In some embodiments, the glycated peptide and/or glycated amino acid are contacted with the fructosyl amino acid oxidase and the peroxidase sequentially or simultaneously. In some embodiments, the FAOD, the peroxidase, and the color forming substance are formulated in a single composition. In some embodiments, the FAOD, the peroxidase, and the color forming substance are formulated in a different composition and are added into the reaction at the same time or at different times.

The percentage of total glycated hemoglobin or percentage of glycated hemoglobin A1c in the blood sample is determined by comparing the signal measured for the amount of $H_2O_2$ (such as the absorbance at around 700 nm for Trinder reaction or the signal measured using an electrochemical biosensor) to a calibration curve. Using the present methods, the percentage of total glycated hemoglobin or percentage of glycated hemoglobin A1c in the blood sample is determined without measuring the total hemoglobin in the blood sample separately. The calibration curve is established using calibrator, i.e., samples (including blood samples and artificial calibrators) with known percentage of glycated hemoglobin or known percentage of glycated hemoglobin A1c. See, e.g., Example 1.

In some embodiments, the calibration curve is prepared by determining signal levels for calibration samples by performing the same steps as the unknown samples without measuring the total hemoglobin separately; and graphing the correlation between the signal levels of the calibration samples and the known percentage of glycated hemoglobin or known percentage of glycated hemoglobin A1c of the calibration samples. For example, whole blood samples having percentages of glycated hemoglobin A1c value assigned by comparison to a suitable higher order reference material can be used as calibrators. Alternative, the percentage of glycated hemoglobin A1c may be determined by another recognized method such as HPLC. Calibrators are tested the same way as the unknown samples using the methods described herein. The absorbance values measured for calibrators are plotted against the expected HbA1c value to establish the calibration curve.

Calibrators other than whole blood sample may also be used to establish a calibration curve. Hemolysate samples (lysed blood samples), glycated peptides, glycated amino acid, and glycated amino acid derivatives in a suitable buffered protein matrix solution having percentage of glycated hemoglobin A1c value assigned by comparison to a suitable higher order reference material can be used as artificial calibrators. For example, calibration samples may be prepared in a phosphate buffered solution with 10% BSA and appropriate amounts of synthesized fructosyl propylamine (glycated amino acid) corresponding to various percentage of HbA1c (e.g., from 5% to 12%). Artificial calibrators are tested the same way as unknown samples except that the lysing step may not be used. The signal measured for the amount of $H_2O_2$ for these calibrators are plotted against the expected HbA1c value to establish the calibration curve. Artificial calibrators may be lyophilized or stabilized for extended shelf life.

The present methods can be used for any suitable purpose. Preferably, the method used in the prognosis or diagnosis of a disease or disorder, e.g., diabetes.

C. Kits for Assaying Percentage of Glycated Hemoglobin

The invention also provides a kit for assaying percentage of total glycated hemoglobin or percentage of glycated hemoglobin A1c without measuring the total hemoglobin separately in a blood sample, said kit comprising: a) a lysing buffer that lyses blood cells to release hemoglobin; b) a first oxidizing agent that selectively oxidizes low molecular weight reducing substances; c) a second oxidizing agent that selectively oxidizes high molecular weight reducing substances; d) a protease that hydrolyzes hemoglobin into protein fragments containing glycated peptides or glycated amino acids; e) a fructosyl amino acid oxidase that reacts with glycated peptides and glycated amino acids to generate hydrogen peroxide ($H_2O_2$); f) a peroxidase and a color forming substance or an electrochemical biosensor for measuring the amount of $H_2O_2$; and g) glycated hemoglobin or glycated hemoglobin A1c calibrator(s) (i.e., calibrator(s) with known percentage of glycated hemoglobin or known percentage of glycated hemoglobin A1c) for use in constructing a calibration curve.

In some embodiments, the first oxidizing agent Dess-Martin periodinane and/or N-ethylmaleimide. In some embodiments, the second oxidizing agent is a tetrazolium salt.

In some embodiments, the lysing buffer contain the first oxidizing agent and/or the second oxidizing agent. In some embodiments, the lysing buffer contains the protease. In some embodiments, the lysing buffer contains the first oxidizing agent, the second oxidizing agent, and the protease. In some embodiments, the first oxidizing agent and the second oxidizing agent are formulated in a single composition. In some embodiments, the first oxidizing agent and the second oxidizing agent are formulated in a separate composition. In some embodiments, the protease is formulated in a single composition with the first oxidizing agent and/or the second oxidizing agent.

The invention also provides a kit for directly assaying percentage of total glycated hemoglobin or percentage of glycated hemoglobin A1c in a blood sample without the need of a separated measurement of total hemoglobin content in blood samples, said kit comprising: a) a lysing buffer that lyses blood cells to release hemoglobin; b) an oxidizing agent, wherein the oxidizing agent is a tetrazolium salt; c) a protease that hydrolyzes hemoglobin into protein fragments containing glycated peptides or glycated amino acids; d) a fructosyl amino acid oxidase that reacts with glycated peptides and glycated amino acids to generate hydrogen peroxide ($H_2O_2$); e) a peroxidase and a color forming substance or an electrochemical biosensor for measuring the amount of $H_2O_2$; and f) calibrator(s) with known percentage of glycated hemoglobin or known percentage of glycated hemoglobin A1c for use in constructing a calibration curve. In some embodiments, the oxidizing agent is contained in the lysing buffer. In some embodiments, the protease is contained in the lysing buffer. In some embodiments, the oxidizing agent and the protease are contained in the lysing buffer. In some embodiments, the protease and oxidizing agent are formulated in a single composition.

In some embodiments, the fructosyl amino acid oxidase and the peroxidase are formulated in a single composition. In some embodiments, the calibrator is a blood sample with known percentage of glycated hemoglobin A1c, which may be in lyophilized form or in solution.

In some embodiments, the kit comprises a lysing buffer, a R1a reagent, a R1b reagent, and a R2 reagent. In some embodiments, the lysing buffer comprises a first oxidizing agent (e.g., N-ethylmaleimide and/or Dess Martin Periodinane). In some embodiments, the R1a reagent comprises a protease and a first oxidizing agent (e.g., N-ethylmaleimide and/or Dess Martin Periodinane). In some embodiments, the R1b reagent comprises a first oxidizing agent (e.g., N-ethylmaleimide and/or Dess Martin Periodinane) and a second oxidizing agent (e.g., a tetrazolium salt). In some embodiments, the R2 reagent comprises a fructosyl amino acid oxidase, a peroxidase (e.g., horseradish peroxidase), and a color forming substance (e.g., DA-64). For examples, the lysing buffer may contain 0.1-10% Triton X-100 (e.g., about 0.1%, about 0.2%, about 0.5%, about 1%, about 2.5%, about 5%, about 7.5%, about 10%); 5-100 mM CHES (e.g., about 5 mM, about 10 mM, about 25 mM, about 50 mM, about 75 mM, about 100 mM), pH about 8.7; 0.1-50 mM N-ethylmaleimide (e.g., about 0.1 mM, about 0.5 mM, about 1 mM, about 5 mM, about 10 mM, about 20 mM, about 30 mM, about 40 mM, about 50 mM); 0.1-5% SDS (e.g., about 0.15%, about 0.25%, about 0.35%, about 0.45%, about 0.55%, about 0.75%, about 1%, about 2.5%, about 5%); 0.001-1 KU/ml catalase (e.g., about 1 U/ml, about 2 U/ml, about 3 U/ml, about 4 U/ml, about 5 U/ml, about 10 U/ml, about 50 U/ml, about 100 U/ml, about 500 U/ml, about 1 KU/ml); 0.001-1 KU/ml ascorbate oxidase (e.g., about 1 U/ml, about 2 U/ml, about 4 U/ml, about 5 U/ml, about 10 U/ml, about 50 U/ml, about 100 U/ml, about 1 KU/ml). The R1a reagent may contain 0.1-10 KU/ml *Bacillus* sp Protease (e.g., about 0.1 KU/ml, about 2 KU/ml, about 3.0 KU/ml, about 3.5 KU/ml, about 4.0 KU/ml, about 4.5 KU/ml, about 5 KU/ml, about 10 KU/ml); 1-100 mM MES (e.g., about 1 mM, about 5 mM, about 10 mM, about 25 mM, about 50 mM, about 100 mM), pH about 7.0; 1-10 mM $CaCl_2$ (e.g., about 1 mM, about 2.5 mM, about 5 mM, about 7.5 mM, about 10 mM); 0.01-10 mM Dess Martin Periodinane (e.g., about 0.01 mM, about 0.015 mM, about 0.02 mM, about 0.05 mM, about 0.1 mM, about 5 mM, about 10 mM); 0.01-5 mg/ml methyl 4-hydroxybenzoate sodium salt (e.g., about 0.01 mg/ml, about 0.05 mg/ml, about 0.1 mg/ml, about 1 mg/ml, about 5 mg/ml); and 0.001-1 mg/ml geneticin (G418) (e.g., about 0.001 mg/ml, about 0.01 mg/ml, about 0.1 mg/ml, about 1 mg/ml). The R1b reagent may contain 0.1-50 mM MES hydrate (e.g., about 0.1 mM, about 0.5 mM, about 1.0 mM, about 10 mM, about 25 mM, about 50 mM); 0.1-50 mM WST-3 (2-(4-Iodopenyl)-3-(2,4-dinitrophenyl)-5-(2,4-disulfophenyl)-2H-tetrazolium, monosodium salt) (e.g., about 0.1 mM, about 0.5 mM, about 1 mM, about 2.5 mM, about 2.6 mM, about 2.7 mM, about 2.8 mM, about 2.9 mM, about 3.0 mM, about 5 mM, about 10 mM, about 25 mM, about 50 mM); and 0.01-10 mM Dess Martin Periodinane (e.g., about 0.01 mM, about 0.04 mM, about 0.05 mM, about 0.06 mM, about 0.07 mM, about 0.08 mM, about 0.09 mM, about 0.1 mM, about 1 mM, about 5 mM, about 10 mM). The R2 reagent may contain 0.01-10 KU/ml fructosyl valine oxidase (e.g., about 0.01 KU/ml, about 0.012 KU/ml, about 0.013 KU/ml, about 0.0135 KU/ml, about 0.014 KU/ml, about 0.0145 KU/ml, about 0.015 KU/ml, about 0.0155 KU/ml, about 0.016 KU/ml, about 0.05 KU/ml, about 0.1 KU/ml, about 1 KU/ml, about 5 KU/ml, about 10 KU/ml); 1-50 mM Tris-HCl (e.g., about 1 mM, about 5 mM, about 10 mM, about 15 mM, about 20 mM, about 50 mM), pH about 8.0; 0.1-10% Triton X-100 (e.g., about 0.1%, about 0.2%, about 0.5%, about 1%, about 2.5%, about 5%, about 7.5%, about 10%); 0.01-10 KU/ml horse radish peroxidase (HRP) (e.g., about 0.01 KU/ml, about 0.05 KU/ml, about 0.08 KU/ml, about 0.09 KU/ml, about 0.1 KU/ml, about 1.0 KU/ml, about 5 KU/ml, about 10 KU/ml); 0.01-10 mM DA-64 (e.g., about 0.01 mM, about 0.05 mM, about 0.075 mM, about 0.08 mM, about 0.085 mM, about 0.09 mM, about 0.1 mM, about 1 mM, about 5 mM, about 10 mM); and 0.01-10 mg/ml geneticin (G418) (e.g., about 0.01 mg/ml, 0.05 mg/ml, about 0.1 mg/ml, about 5 mg/ml, about 10 mg/ml). The kit may further comprise instructions to practice methods described herein. The kit may be used in described in detail in Example 1.

The kits of the invention may be in any suitable packaging. Suitable packaging includes, but is not limited to, vials, bottles, jars, flexible packaging, and the like. Kits may further comprise instructions for practicing any of the methods described herein.

EXAMPLES

Example 1

Single Channel HbA1c Enzymatic Assay

This single channel HbA1c test is an enzymatic assay in which samples are lysed and reacted with agents to eliminate low molecular weight and high molecular weight signal interfering substances. The lysed whole blood samples are subjected to extensive protease digestion with *Bacillus* sp protease. This process releases amino acids including glycated valine from the hemoglobin beta chains. Glycated valine is then served as a substrate for specific recombinant fructosyl valine oxidase (FVO) enzyme, produced in *E. coli*. The recombinant FVO specifically can cleave N-terminal valine and produce hydrogen peroxide in the presence of selective agents. This, in turn, is measured using a horse radish peroxidase (POD) catalyzed reaction and a suitable chromagen. The HbA1c concentration is expressed directly as % HbA1c by use of a suitable calibration curve.

I. Reagent Compositions.

Lysis buffer: 50 mM CHES pH 9.4, 2% Triton X-100, 3 mM Dess-Martin Periodinane, and 2.5 mM N-ethyl Maleimide.

Reagent R1a: 25 mM MES buffer pH 6.5, 5 mM $CaCl_2$, 1000 U/ml neutral protease (Toyobo Co., Ltd.), 2 mM N-ethyl Maleimide.

Reagent R1b: 25 mM MES pH 6.5, 150 mM sodium chloride, 5 mM Dess-Martin Periodinane, 2 mM WST3 (2-(4-Iodopenyl)-3-(2,4-dinitrophenyl)-5-(2,4-disulfophenyl)-2H-tetrazolium, monosodium salt (manufactured by Dojindo Laboratories)).

Reagent R2: 25 mM Tris, pH 8.2, 5 U/ml fructosyl amino acid oxidase having the amino acid sequence shown in SEQ ID NO:1, 50 U/ml Horse Radish Peroxidase, and 0.5 mM chromagen (N-(carboxymethylaminocarbonyl)-4,4'-bis (dimethylamino) diphenylamine sodium salt (product name DA-64, manufactured by Wako).

II. Assay Procedure

Lysis buffer (500 μL) was dispensed in a suitable container such as a sample cup or an eppendorf microfuge tube. Prior to testing, whole blood samples were mixed by gentle inversion to resuspend settled erythrocytes. Fully resuspended whole blood sample (40 μL) was mixed gently with the lysis buffer using a suitable pipettor without creating foam. The mixture was then incubated for 5 to 10 minutes at room temperature. Complete lysis was observed when the mixture became a clear red solution without any particulate matter.

Reagents R1a and R1b were mixed in 70:30 volume ratio prior to use. Reagent R1b was poured into R1a, and the reagents were mixed gently by inversion to form Reagent R1ab.

Figure 2:
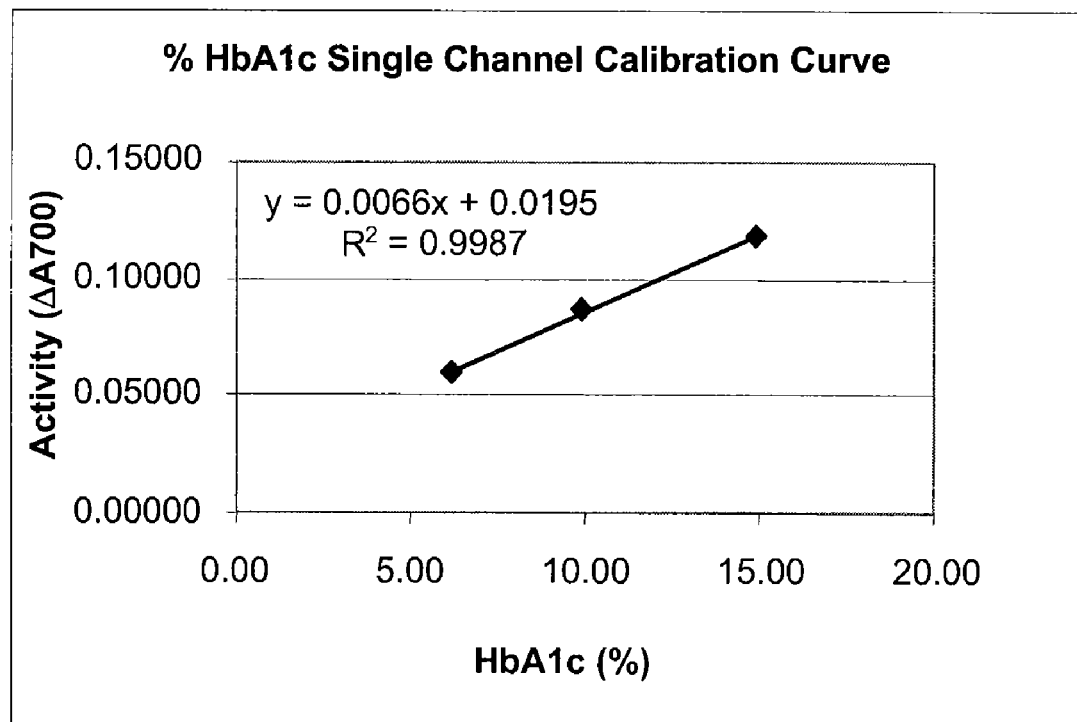
FIG. 2 shows a calibration curve for enzymatic HbA1c assay. X-axis shows percentage of glycated hemoglobin A1c known for the calibration sample; and Y-axis shows the corresponding difference in absorbance value at 700 nm between 8 min and 5 min after adding reagent R1a and R1b.

Reagent R1ab (170 μL) and lysate (20 μL) were added into a cuvette, and mixed. The cuvette was incubated at 37° C. for 5 minutes. The reaction can also be carried out at room temperature. After the incubation, 50 μL of Reagent R2 was added into the cuvette. The absorbance at 700 nm was monitored for 3 minutes. The absorbance value was calculated for calibrators, controls and samples by subtracting O.D. value at A2 (absorbance at 3 min after the addition of R2) from O.D.

value at A1 (absorbance right after the addition of R2), i.e., ΔA700=(A2−A1). The timeline of the reaction is shown in FIG. 1. Values of unknown samples were determined by use of a calibration curve shown, e.g., in FIG. 2 which was represented directly in HbA1c % units.

The calibration curve (FIG. 2) was prepared using data from measuring ΔA700 for three standard samples with known percentage of glycated hemoglobin A1c (6.25%, 10.00%, and 15.00%) following the procedure described above. The calibrators were prepared by testing suitable whole blood material for HbA1c values using HPLC method. The whole blood material used for calibration could be lyophilized or stabilized for extended shelf life.

As shown in Table 2, the value of percentage of glycated hemoglobin A1c obtained using the method described above (column under "obtained value") correlates with expected value in the sample. The expected value for a sample was obtained from HPLC. The ranges for the expected value indicate acceptable value ranges.

TABLE 2

| | HbA1c (%) | |
|---|---|---|
| Samples | Expected Value (HPLC) | Obtained Value |
| 1 | 6.2 (5.27-7.13) | 6.84 |
| 2 | 12.2 (10.37-14.03) | 12.13 |
| 3 | 5.9 (5.0-6.8) | 5.15 |
| 4 | 11.1 (9.4-12.7) | 11.18 |
| 5 | 5.4 | 5.21 |
| 6 | 9.1 | 9.30 |
| 7 | 5.4 | 5.71 |
| 8 | 9.0 | 9.17 |

III. Precision of the Single Channel Enzymatic Hemoglobin A1c Assay

The within-run precision was evaluated with two different % HbA1c level fresh whole blood samples (sample ID 10810285 low HbA1c and sample ID 10810244 high HbA1c) replicated 16 times. The evaluation was done using the Hitachi 917 auto-analyzer instrument and the single channel enzymatic hemoglobin A1c assay described in this example. Normal Control and pathonormal controls were included in the study.

The whole blood samples with verified % HbA1c values used for this study were obtained from a certified commercial source, ProMedDx, LLC (10 Commerce Way, Norton, Mass. 02766) and came with an IRB certification that protocols, informed consent, used to collect samples were IRB approved.

Table 3 below shows the precision of the single channel enzymatic hemoglobin A1c assay.

TABLE 3

| | ID 10810285 (% HbA1c) | ID 10810244 (% HbA1c) |
|---|---|---|
| Mean value | 4.8% | 8.2% |
| Intra run SD | 0.07 | 0.05 |
| Intra run CV % | 1.4% | 0.6% |

IV. Accuracy of the Single Channel Enzymatic Hemoglobin A1c Assay

To demonstrate accuracy, the single channel enzymatic hemoglobin A1c assay was used with individual whole blood samples (ID series depicted below) and compared to Tosoh's HbA1c HPLC assay, which is the currently marketed HbA1c device (Tosoh G7: HbA1c Variant Analysis Mode). The accuracy study tests were performed on the Hitachi 917 Autoanalyzer instrument.

The whole blood samples with verified HbA1c values used for this study were from a certified commercial source, ProMedDx, LLC and came with an IRB certification that protocols, informed consent, used to collect samples were IRB approved.

The comparison study included 30 test samples and the results obtained are shown in Table 4 below. "Tosoh % HbA1c" indicates values obtained using Tosoh's HbA1c HPLC method for the samples. "DZ % HbA1c" indicates corresponding values obtained using the single channel enzymatic hemoglobin A1c assay described in this example.

TABLE 4

| | Fresh Whole Blood Sample ID | Tosoh % HbA1c | DZ % HbA1c |
|---|---|---|---|
| 1 | 10810257 | 4.9 | 5.1 |
| 2 | 10897226 | 5.1 | 5.4 |
| 3 | 10897227 | 5.1 | 5.1 |
| 4 | 10897229 | 5.2 | 5.4 |
| 5 | 10897230 | 5.3 | 5.2 |
| 6 | 10845039 | 8.7 | 8.4 |
| 7 | 10845043 | 8.5 | 8.7 |
| 8 | 10845044 | 7.1 | 6.8 |
| 9 | 10845045 | 7.8 | 7.5 |
| 10 | 10845059 | 6.9 | 6.8 |
| 11 | 10810281 | 10.9 | 11.7 |
| 12 | 10897261 | 9.6 | 10.0 |
| 13 | 10897272 | 10.1 | 10.9 |
| 14 | 10897278 | 14.4 | 15.6 |
| 15 | 10897231 | 5.6 | 5.6 |
| 16 | 10897234 | 5.7 | 5.8 |
| 17 | 10897238 | 5.4 | 5.4 |
| 18 | 10897239 | 5.7 | 5.9 |
| 19 | 10897241 | 5.4 | 5.3 |
| 20 | 10845060 | 7.6 | 7.4 |
| 21 | 10845063 | 8.1 | 7.3 |
| 22 | 10845065 | 6.4 | 6.4 |
| 23 | 10845066 | 6.5 | 6.6 |
| 24 | 10845068 | 6.7 | 6.3 |
| 25 | 10897285 | 10.8 | 9.7 |
| 26 | 10897286 | 9.9 | 10.4 |
| 27 | 10897290 | 9.7 | 8.7 |
| 28 | 10897295 | 9.6 | 9.8 |
| 29 | DZ Ctl L1 Lot CON100405B-1 | 5.3 | 5.4 |
| 30 | DZ Ctl L2 Lot CON200405B-1 | 10.9 | 10.9 |

Figure 3:
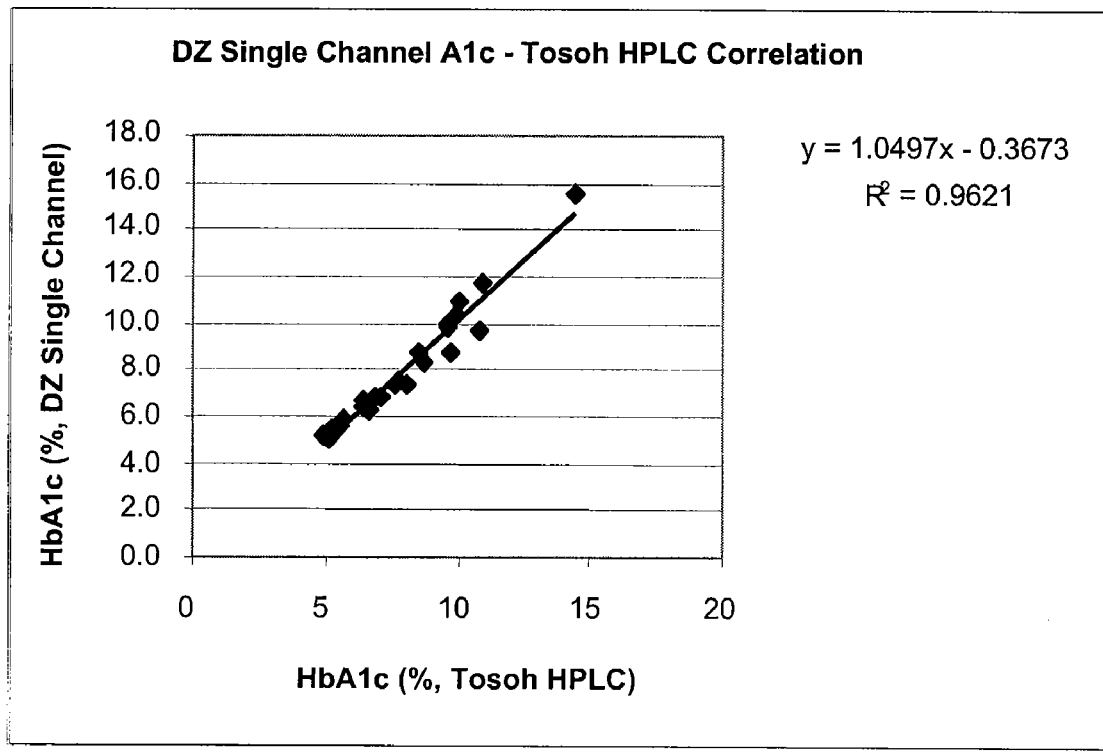
FIG. 3 shows the correlation between the single channel enzymatic hemoglobin A1c assay described in Example 1 and Tosoh's HPLC method. Y axis shows the HbA1c value measured using the single channel enzymatic hemoglobin A1c assay described in Example 1 for samples; and X-axis shows HbA1c value measured using the Tosoh HPLC method for the corresponding samples.

FIG. 3 shows the HbA1c value (%) obtained using the single channel enzymatic hemoglobin A1c assay described in this example plotted against results obtained with Tosoh's HPLC methods. As shown in FIG. 3, the slope was 1.05; the correlation coefficient between the two methods was 0.96; and the y intercept was −0.367.

Example 2

Single Channel HbA1c Enzymatic Assay Using One Oxidizing Agent

The procedures of single channel HbA1c test in this example were similar to the procedures described in Example 1 except only one oxidizing agent was used for oxidizing reducing substances in the blood samples.

I. Reagent Compositions
  Lysis buffer: 50 mM CHES pH 9.4, and 2% Triton X-100.
  Reagent R1a: 25 mM MES buffer pH 6.5, 5 mM $CaCl_2$, 1000 U/ml neutral protease (Toyobo Co., Ltd.).
  Reagent R1b: 25 mM MES pH 6.5, 150 mM sodium chloride, and 2 mM WST3 (2-(4-Iodopenyl)-3-(2,4-dinitrophenyl)-5-(2,4-disulfophenyl)-2H-tetrazolium, monosodium salt (manufactured by Dojindo Laboratories)).

Reagent R2: 25 mM Tris, pH 8.2, 5 U/ml fructosyl amino acid oxidase having the amino acid sequence shown in SEQ ID NO:1, 50 U/ml Horse Radish Peroxidase, and 0.5 mM chromagen (N-(carboxymethylaminocarbonyl)-4,4'-bis (dimethylamino) diphenylamine sodium salt (product name DA-64, manufactured by Wako).

II. Assay Procedure

Lysis buffer (500 μL) was dispensed in a suitable container such as a sample cup or an eppendorf microfuge tube. Prior to testing, whole blood samples were mixed by gentle inversion to resuspend settled erythrocytes. Fully resuspended whole blood sample (40 μL) was mixed gently with the lysis buffer using a suitable pipettor without creating foam. The mixture was then incubated for 5 to 10 minutes at room temperature. Complete lysis was observed when the mixture became a clear red solution without any particulate matter.

Reagents R1a and R1b were mixed in 70:30 volume ratio prior to use. Reagent R1b was poured into R1a, and the reagents were mixed gently by inversion to form Reagent R1ab.

Reagent R1ab (170 μL) and lysate (20 μL) were added into a cuvette, and mixed. The cuvette was incubated at 37° C. for 5 minutes. After the incubation, 50 μL of Reagent R2 was added into the cuvette. The absorbance at 700 nm was monitored for 3 minutes. The absorbance value was calculated for calibrators, controls and samples by subtracting O.D. value at A2 (absorbance at 3 min after the addition of R2) from O.D. value at A1 (absorbance right after the addition of R2), i.e., ΔA700=(A2−A1). The timeline of the reaction is shown in FIG. 1.

Figure 4:
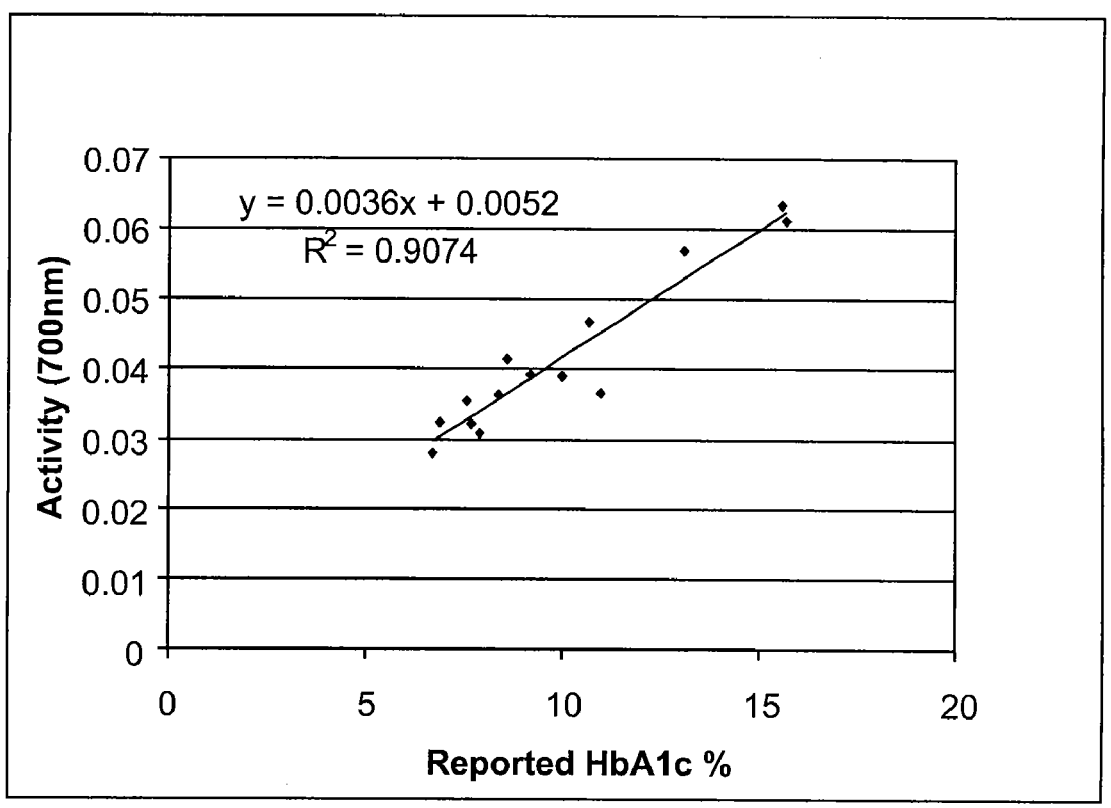
FIG. 4 shows a calibration curve for enzymatic HbA1c assay using one oxidizing agent as described in Example 2. X-axis shows percentage of glycated hemoglobin A1c known for the calibration sample; and Y-axis shows the corresponding difference in absorbance value at 700 nm between 8 min and 5 min after adding reagent R1a and R1b.

FIG. 4 shows the data from measuring ΔA700 (Y-axis) for the samples following the procedure described above plotted against known percentage of glycated hemoglobin A1c. FIG. 4 indicates that percentage of glycated hemoglobin A1c can also be determined directly without a separate measurement of total hemoglobin using a reagent system with a single oxidizing agent tetrazolium, though the results (accuracy and correlation) were not as good as those obtained with a reagent system with two oxidizing agents as described in Example 1.

Although the foregoing invention has been described in some detail by way of illustration and example for purposes of clarity and understanding, it will be apparent to those skilled in the art that certain changes and modifications may be practiced. Therefore, descriptions and examples should not be construed as limiting the scope of the invention, which is delineated by the appended claims.

The claimed invention is:

1. A method for directly assaying percentage of glycated hemoglobin A1c in a blood sample without measuring the total hemoglobin in the blood sample in a separate process, said method comprising:
   a) contacting protein fragments containing glycated peptides or glycated amino acids with a fructosyl amino acid oxidase to generate hydrogen peroxide ($H_2O_2$), wherein the protein fragments are generated by contacting the blood sample with 1) a lysing buffer which releases hemoglobin from red blood cells in the blood sample; 2) an oxidizing agent which is a tetrazolium salt, and 3) a protease which digests glycated hemoglobin into the glycated peptides or glycated amino acids and generates glycated glycine, glycated valine, glycated lysine residue, or a glycated peptide comprising glycated glycine, glycated valine or glycated lysine residue; and wherein the fructosyl amino acid oxidase comprises the amino acid sequence set forth in SEQ ID NO:1;
   b) measuring the amount of $H_2O_2$ generated in step a); and
   c) determining percentage of glycated hemoglobin A1c in the sample by correlating the measured value in step b) to a percentage of glycated hemoglobin A1c in a calibration curve without measuring the total hemoglobin in the blood sample separately.

2. The method of claim 1, wherein the amount of $H_2O_2$ generated in step a) is measured by an electrochemical biosensor to generate a measurable signal.

3. The method of claim 1, wherein the lysing buffer contains the oxidizing agent.

4. The method of claim 1 or 3, wherein the lysing buffer contains the protease.

5. The method of claim 1, wherein the oxidizing agent and the protease are formulated in a single composition.

6. The method of claim 1, wherein tetrazolium salt is 2-(4-iodophenyl) -3-(2,4-dinitrophenyl)-5-(2,4-disulfophenyl)-2H-tetrazolium monosodium salt or 2-(4-iodophenyl) -3-(4-nitrophenyl)-5-(2,4-disulfophenyl)-2H-tetrazolium monosodium salt.

7. The method of claim 1, wherein the blood sample is a whole blood.

8. The method of claim 1, wherein the protease is an endo-type protease or an exo-type protease.

9. The method of claim 1, wherein the protease is selected from the group consisting of proteinase K, pronase E, ananine, thermolysin, subtilisin and cow pancreas proteases.

10. The method of claim 1, wherein the protease is a neutral protease of *Aspergillus* or *Bacillus* origin.

11. The method of claim 1, wherein the protease generates a glycated peptide from about 2 to about 30 amino acid residues.

12. The method of claim 1, further comprising using the percentage of glycated hemoglobin A1c for prognosing or diagnosing a disease or disorder.

* * * * *

SEQUENCE LISTING

```
<160> NUMBER OF SEQ ID NOS: 1

<210> SEQ ID NO 1
<211> LENGTH: 472
<212> TYPE: PRT
<213> ORGANISM: Artificial Sequence
<220> FEATURE:
<223> OTHER INFORMATION: Fructosyl amino acid oxidase

<400> SEQUENCE: 1

Met Gly Gly Ser Gly Asp Asp Asp Asp Leu Ala Leu Ala Val Thr Lys
1               5                   10                  15

Ser Ser Ser Leu Leu Ile Val Gly Ala Gly Thr Trp Gly Thr Ser Thr
            20                  25                  30

Ala Leu His Leu Ala Arg Arg Gly Tyr Thr Asn Val Thr Val Leu Asp
        35                  40                  45

Pro Tyr Pro Val Pro Ser Ala Ile Ser Ala Gly Asn Asp Val Asn Lys
    50                  55                  60

Val Ile Ser Ser Gly Gln Tyr Ser Asn Asn Lys Asp Glu Ile Glu Val
65                  70                  75                  80

Asn Glu Ile Leu Ala Glu Glu Ala Phe Asn Gly Trp Lys Asn Asp Pro
                85                  90                  95

Leu Phe Lys Pro Tyr Tyr His Asp Thr Gly Leu Leu Met Ser Ala Cys
            100                 105                 110

Ser Gln Glu Gly Leu Asp Arg Leu Gly Val Arg Val Arg Pro Gly Glu
        115                 120                 125

Asp Pro Asn Leu Val Glu Leu Thr Arg Pro Glu Gln Phe Arg Lys Leu
    130                 135                 140

Ala Pro Glu Gly Val Leu Gln Gly Asp Phe Pro Gly Trp Lys Gly Tyr
145                 150                 155                 160

Phe Ala Arg Ser Gly Ala Gly Trp Ala His Ala Arg Asn Ala Leu Val
                165                 170                 175

Ala Ala Ala Arg Glu Ala Gln Arg Met Gly Val Lys Phe Val Thr Gly
            180                 185                 190
```

-continued

```
Thr Pro Gln Gly Arg Val Val Thr Leu Ile Phe Glu Asn Asn Asp Val
        195                 200                 205

Lys Gly Ala Val Thr Gly Asp Gly Lys Ile Trp Arg Ala Glu Arg Thr
        210                 215                 220

Phe Leu Cys Ala Gly Ala Ser Ala Gly Gln Phe Leu Asp Phe Lys Asn
225                 230                 235                 240

Gln Leu Arg Pro Thr Ala Trp Thr Leu Val His Ile Ala Leu Lys Pro
                245                 250                 255

Glu Glu Arg Ala Leu Tyr Lys Asn Ile Pro Val Ile Phe Asn Ile Glu
                260                 265                 270

Arg Gly Phe Phe Glu Pro Asp Glu Glu Arg Gly Glu Ile Lys Ile
        275                 280                 285

Cys Asp Glu His Pro Gly Tyr Thr Asn Met Val Gln Ser Ala Asp Gly
        290                 295                 300

Thr Met Met Ser Ile Pro Phe Glu Lys Thr Gln Ile Pro Lys Glu Ala
305                 310                 315                 320

Glu Thr Arg Val Arg Ala Leu Leu Lys Glu Thr Met Pro Gln Leu Ala
                325                 330                 335

Asp Arg Pro Phe Ser Phe Ala Arg Ile Cys Trp Cys Ala Asp Thr Ala
                340                 345                 350

Asn Arg Glu Phe Leu Ile Asp Arg His Pro Gln Tyr His Ser Leu Val
        355                 360                 365

Leu Gly Cys Gly Ala Ser Gly Arg Gly Phe Lys Tyr Leu Pro Ser Ile
370                 375                 380

Gly Asn Leu Ile Val Asp Ala Met Glu Gly Lys Val Pro Gln Lys Ile
385                 390                 395                 400

His Glu Leu Ile Lys Trp Asn Pro Asp Ile Ala Ala Asn Arg Asn Trp
                405                 410                 415

Arg Asp Thr Leu Gly Arg Phe Gly Gly Pro Asn Arg Val Met Asp Phe
                420                 425                 430

His Asp Val Lys Glu Trp Thr Asn Val Gln Tyr Arg Asp Ile Ser Lys
        435                 440                 445

Leu Lys Gly Glu Leu Glu Gly Leu Pro Ile Pro Asn Pro Leu Leu Arg
        450                 455                 460

Thr Gly His His His His His His
465                 470
```